United States Patent
Li et al.

(10) Patent No.: US 10,851,408 B2
(45) Date of Patent: Dec. 1, 2020

(54) METHODS AND KITS FOR DETECTING GENE MUTATIONS

(71) Applicant: Shuwen Biotech Co. Ltd., Deqing, Zhengjiang Province (CN)

(72) Inventors: Xingmin Li, Deqing (CN); Huanhuan Yang, Deqing (CN)

(73) Assignee: SHUWEN BIOTECH CO. LTD., Deqing (CN)

( * ) Notice: Subject to any disclaimer, the term of this patent is extended or adjusted under 35 U.S.C. 154(b) by 45 days.

(21) Appl. No.: 16/235,969

(22) Filed: Dec. 28, 2018

(65) Prior Publication Data

US 2019/0203261 A1   Jul. 4, 2019

(51) Int. Cl.
| | |
|---|---|
| *C12Q 1/686* | (2018.01) |
| *C12Q 1/6853* | (2018.01) |
| *C12Q 1/6806* | (2018.01) |
| *C12Q 1/6886* | (2018.01) |
| *C12Q 1/6858* | (2018.01) |

(52) U.S. Cl.
CPC .......... *C12Q 1/686* (2013.01); *C12Q 1/6806* (2013.01); *C12Q 1/6853* (2013.01); *C12Q 1/6858* (2013.01); *C12Q 1/6886* (2013.01); *C12Q 2600/112* (2013.01); *C12Q 2600/156* (2013.01)

(58) Field of Classification Search
CPC ........ C12Q 2521/101; C12Q 2521/107; C12Q 1/686
See application file for complete search history.

(56) References Cited

U.S. PATENT DOCUMENTS

| | | | |
|---|---|---|---|
| 6,063,568 A * | 5/2000 | Gerdes ................. | C12Q 1/6851 435/6.11 |
| 2017/0051332 A1 * | 2/2017 | Wu ........................ | C12Q 1/686 |

* cited by examiner

*Primary Examiner* — Teresa E Strzelecka
(74) *Attorney, Agent, or Firm* — Stoel Rives LLP (57) ABSTRACT

The invention relates to methods, kits and uses thereof for detecting gene mutations. The method comprises the step of: providing a mixture of nucleic acid molecules comprising both a genomic DNA and a RNA molecule derived from said genomic DNA, performing a reverse transcription reaction with a reverse transcriptase to provide cDNA molecules from said RNA molecule in said mixture; and performing PCR using both said genomic DNA and said cDNA molecules as templates. This method can simultaneously detect a trace amount of a mutation in both DNA and RNA from a whole blood sample using a small amount of sample. At the same time, by adjusting the reaction system, the detection limit of a mutant in a background of wild-type molecules can reach 0.01% or lower.

6 Claims, 6 Drawing Sheets
Specification includes a Sequence Listing.

SEQUENCE LISTING

<160> NUMBER OF SEQ ID NOS: 20

<210> SEQ ID NO 1
<211> LENGTH: 72
<212> TYPE: DNA
<213> ORGANISM: Artificial Sequence
<220> FEATURE:
<223> OTHER INFORMATION: Partial Sequence of EGFR

<400> SEQUENCE: 1
ccaccgtgca gctcatcatg cagctcatgc ccttcggctg cctcctggac tatgtccggg     60
aacacaaaga ca                                                         72

<210> SEQ ID NO 2
<211> LENGTH: 19
<212> TYPE: DNA
<213> ORGANISM: Artificial Sequence
<220> FEATURE:
<223> OTHER INFORMATION: ARMS F1 Primer

<400> SEQUENCE: 2
ccaccgtgca gctcataat                                                  19

<210> SEQ ID NO 3
<211> LENGTH: 18
<212> TYPE: DNA
<213> ORGANISM: Artificial Sequence
<220> FEATURE:
<223> OTHER INFORMATION: R1 Primer

<400> SEQUENCE: 3
tgtctttgtt tcccggac                                                   18

<210> SEQ ID NO 4
<211> LENGTH: 15
<212> TYPE: DNA
<213> ORGANISM: Artificial Sequence
<220> FEATURE:
<223> OTHER INFORMATION: T790M Probe

<400> SEQUENCE: 4
gctcatgccc ttcgg                                                      15

<210> SEQ ID NO 5
<211> LENGTH: 19
<212> TYPE: DNA
<213> ORGANISM: Artificial Sequence
<220> FEATURE:
<223> OTHER INFORMATION: T790M Blocker

<400> SEQUENCE: 5
caccgtgcag ctcatcacg                                                  19

<210> SEQ ID NO 6
<211> LENGTH: 16
<212> TYPE: DNA
<213> ORGANISM: Artificial Sequence
<220> FEATURE:
<223> OTHER INFORMATION: CK1 F Primer

<400> SEQUENCE: 6
aaatcctgca tggcgc                                                     16

<210> SEQ ID NO 7
<211> LENGTH: 18

```
<212> TYPE: DNA
<213> ORGANISM: Artificial Sequence
<220> FEATURE:
<223> OTHER INFORMATION: CK R1 primer

<400> SEQUENCE: 7
gccactggat gctctcca                                                    18

<210> SEQ ID NO 8
<211> LENGTH: 17
<212> TYPE: DNA
<213> ORGANISM: Artificial Sequence
<220> FEATURE:
<223> OTHER INFORMATION: CK1 Probe

<400> SEQUENCE: 8
aacaaccctg ccctgtg                                                     17

<210> SEQ ID NO 9
<211> LENGTH: 19
<212> TYPE: DNA
<213> ORGANISM: Artificial Sequence
<220> FEATURE:
<223> OTHER INFORMATION: AMRS F2 Primer

<400> SEQUENCE: 9
ccaccgtgca gctcatcat                                                   19

<210> SEQ ID NO 10
<211> LENGTH: 23
<212> TYPE: DNA
<213> ORGANISM: Artificial Sequence
<220> FEATURE:
<223> OTHER INFORMATION: R2 Primer

<400> SEQUENCE: 10
ccgtatctcc cttccctgat tac                                              23

<210> SEQ ID NO 11
<211> LENGTH: 85
<212> TYPE: DNA
<213> ORGANISM: Artificial Sequence
<220> FEATURE:
<223> OTHER INFORMATION: Pritial Sequence of BRAF

<400> SEQUENCE: 11
ggtgattttg gtctagctac agagaaatct cgatggagtg ggtcccatca gtttgaacag      60
ttgtctggat ccattttgtg gatgg                                            85

<210> SEQ ID NO 12
<211> LENGTH: 23
<212> TYPE: DNA
<213> ORGANISM: Artificial Sequence
<220> FEATURE:
<223> OTHER INFORMATION: ARMS F3 Primer

<400> SEQUENCE: 12
ggtgattttg gtctagctac tga                                              23

<210> SEQ ID NO 13
<211> LENGTH: 23
<212> TYPE: DNA
<213> ORGANISM: Artificial Sequence
<220> FEATURE:
<223> OTHER INFORMATION: R3 Primer
```

-continued

<400> SEQUENCE: 13
ccatccacaa aatggatcca gac                                          23

<210> SEQ ID NO 14
<211> LENGTH: 18
<212> TYPE: DNA
<213> ORGANISM: Artificial Sequence
<220> FEATURE:
<223> OTHER INFORMATION: V600E Probe

<400> SEQUENCE: 14
atggagtggg tcccatca                                                18

<210> SEQ ID NO 15
<211> LENGTH: 27
<212> TYPE: DNA
<213> ORGANISM: Artificial Sequence
<220> FEATURE:
<223> OTHER INFORMATION: V600E Blocker

<400> SEQUENCE: 15
ggtgattttg gtctagctac agtgaaa                                      27

<210> SEQ ID NO 16
<211> LENGTH: 25
<212> TYPE: DNA
<213> ORGANISM: Artificial Sequence
<220> FEATURE:
<223> OTHER INFORMATION: CK2 F Primer

<400> SEQUENCE: 16
gtggaatatc aaacaaatga ttaag                                        25

<210> SEQ ID NO 17
<211> LENGTH: 21
<212> TYPE: DNA
<213> ORGANISM: Artificial Sequence
<220> FEATURE:
<223> OTHER INFORMATION: CK2 R Primer

<400> SEQUENCE: 17
attgatggtg gattatgctc c                                            21

<210> SEQ ID NO 18
<211> LENGTH: 20
<212> TYPE: DNA
<213> ORGANISM: Artificial Sequence
<220> FEATURE:
<223> OTHER INFORMATION: CK2 Probe

<400> SEQUENCE: 18
acacaggaac atatagaggc                                              20

<210> SEQ ID NO 19
<211> LENGTH: 23
<212> TYPE: DNA
<213> ORGANISM: Artificial Sequence
<220> FEATURE:
<223> OTHER INFORMATION: ARMS F4 Primer

<400> SEQUENCE: 19
ggtgattttg gtctagctac aga                                          23

<210> SEQ ID NO 20
<211> LENGTH: 25

```
<212> TYPE: DNA
<213> ORGANISM: Artificial Sequence
<220> FEATURE:
<223> OTHER INFORMATION: R4 Primer

<400> SEQUENCE: 20
cttaccatcc acaaaatgga tccag                                          25
```

METHODS AND KITS FOR DETECTING GENE MUTATIONS

RELATED APPLICATIONS

This application claims priority to China Patent Application No. 201811138710.5, titled "KITS, METHODS AND USES THEREOF BASED ON CODAR-ARMS-PCR FOR DETECTING GENE MUTATIONS," filed Sep. 28, 2018 and China Patent Application No. 201711454492.1, titled "KITS, METHODS AND USES THEREOF BASED ON CODAR-PCR FOR DETECTING GENE MUTATIONS," filed Dec. 28, 2017, both of which are hereby incorporated herein by reference to the extent such subject matter is not inconsistent herewith.

Field of the Invention

The invention relates to detection kits, methods and uses thereof, in particular to kits, methods and uses thereof for detecting gene mutations.

Background of the Invention

Genetic mutations are DNA sequence changes on a chromosome, such as replacements, additions or deletions of DNA base pairs in a long chain of chromosomal DNA. Mutations are the basis of biological evolution and genetic diversity. At the same time, however, it is also the direct cause of most human genetic diseases, tumors and other susceptible diseases. In particular, some somatic mutations are the hallmarks of tumor DNA. Thus, detecting such mutations in tumor tissues or circulating tumor DNA has become part of the mainstream tumor treatment process. In many cases, tumor tissue samples are unavailable for use in mutation detection, and circulating tumor DNA is rather rare in patient blood. While there has been much effort in the field in detecting mutations using circulating tumor DNA from plasma samples, it remains challenging because mutant DNA is extremely rare in plasma compared to wild-type DNA.

At present, methods suitable for detecting low-concentration mutant DNA primarily include digital PCR (dPCR), next generation sequencing (NGS), and amplification refractory mutation System (ARMS). Although the digital PCR method has the advantages of high sensitivity, high precision, and absolute quantification, it is not easy to use and requires special equipment generally unavailable in hospitals. The NGS technology also has its shortcomings. The cost is high, and it requires lengthy time and much lab and computational work. The ARMS method is commonly used. But its sensitivity is not high enough for it to be suitable for detecting low amounts of circulating mutant tumor DNA in a background of wild-type plasma DNA.

SUMMARY OF THE INVENTION

In order to solve at least one of the above technical problems, a first aspect of the present invention provides a method for detecting a mutation in a biological sample. Generally, in the method of the invention, a mixture of nucleic acid molecules is provided which contains both genomic DNA molecules, and RNA molecules derived from the genomic DNA. Both the genomic DNA and the RNA molecule are extracted from a human whole blood sample from a cancer patient. A reverse transcription reaction is performed on the RNA molecules in the mixture using a reverse transcriptase to generate cDNA molecules from the RNA molecules. Both the genomic DNA and the cDNA molecules are used as templates PCR amplification and detection of the presence or absence of one or more mutations in the molecules.

Generally speaking, the whole blood sample from a cancer patient may include red blood cells, platelets, and exosomes. But it may also include white blood cells, circulating cell free DNA (cfDNAs), circulating cell free RNA, circulating tumor cells (CTCs), circulating tumor DNA (ctDNAs), circulating tumor RNA (ctRNA). In one embodiment, white blood cells are removed artificially from the blood sample, and thus the whole blood sample is depleted or free of white blood cells.

A second aspect of the present invention provides a PCR reaction mixture. The PCR reaction mixture comprises a mixture of nucleic acid molecules having both a genomic DNA of a human gene and a RNA molecule derived from the genomic DNA. Both the genomic DNA and the RNA molecule are extracted from a human whole blood sample from a cancer patient. The PCR reaction mixture further contains a reverse transcriptase, a Taq DNA polymerase, and a pair of PCR primers.

A third aspect of the present invention provides a kit for detecting a gene mutation in a biological sample. The kit comprises a first primer pair capable of amplifying by PCR a DNA sequence of a gene; a RT primer for priming reverse transcription from a RNA transcript of the DNA sequence to provide a cDNA; a second primer pair capable of amplifying by PCR all or part of said cDNA sequence; and an enzyme mixture having both a reverse transcriptase and a Taq polymerase.

The foregoing and other advantages and features of the invention, and the manner in which the same are accomplished, will become more readily apparent upon consideration of the following detailed description of the invention taken in conjunction with the accompanying examples and drawings, which illustrate preferred or exemplary embodiments.

DETAILED DESCRIPTION OF THE INVENTION

The invention establishes a method for detecting mutations of a gene in various types of biological sample with high sensitivity and specificity. The method is especially suitable for samples in which mutant is at a very low level in a background of wild-type. For example, the method may be used in detecting low level of tumor-specific mutations in a high background of wild-type DNA or RNA, such as in liquid biopsy.

Specifically, in accordance with the first aspect of the invention, a method is provided for detecting a mutation in a sample. The method comprises the steps of:

providing a mixture of nucleic acid molecules containing both a genomic DNA and RNA molecules derived from the genomic DNA; performing a reverse transcription reaction with a reverse transcriptase to provide cDNA molecules from the RNA molecules in the mixture; and performing PCR using both the genomic DNA and the cDNA molecules as templates. In the method, both the genomic DNA and the RNA molecules are extracted from a biological sample.

In some embodiments, the method is used for detecting a tumor-specific mutation in a cancer patient sample, e.g., a tumor tissue sample, a plasma sample, a whole blood sample, an ascites sample, a urine sample, a saliva sample, a tear sample, etc. Preferably, all nucleic acids including both DNA and RNA are extracted from the biological sample, and the nucleic acid mixture resulting from the extraction would include both a DNA sequence of a gene and the corresponding RNA molecules transcribed from the DNA sequence.

When a whole blood sample of a cancer patient is used as the biological sample, it typically contains red blood cells, white blood cells, platelets, exosomes, circulating cell free DNA (ccfDNA), circulating cell free RNA (ccfRNA), and circulating tumor cells (CTCs). A small portion of the circulating cell free DNA may be circulating tumor DNA (ctDNAs). Similarly, the circulating cell free RNA may include circulating tumor RNA (ctRNA). Thus, mutant DNA and RNA molecules derived from tumor may be among the circulating cell free DNA and RNA, or reside in exosomes, platelets, CTCs or other cells. The CTCs may be freely floating in the whole blood sample or reside in one of other types cells through endocytosis. Thus, "the mixture of nucleic acid molecules" containing both a genomic DNA and RNA molecules derived from the genomic DNA as recited above may be extracted from the whole blood samples to include such genomic DNA and RNA molecules.

In some embodiments of the present invention, the whole blood sample is free of white blood cells. White blood cells may be removed from the whole blood sample by techniques known in the art.

In accordance with the method of the present invention, the RNA molecules in the mixture of nucleic acid molecules may be used as templates for making complementary DNA (cDNA) through reverse transcription reactions under the catalysis of reverse transcriptase. Reverse transcription in vitro is generally known in the art. It may require a reverse transcription primer hybridizing to a sequence of the RNA molecule to prime the incorporation of deoxynucleotides and synthesis of cDNA through reverse transcription.

The resulting cDNA and the corresponding genomic DNA may be both used as templates for PCR amplification and detection of mutations. In this regard, one or more primer pairs including a forward primer and a reverse primer may be used for PCR amplification of a sequence of the above genomic DNA and/or cDNA. In one embodiment, the method may further comprise the step of determining whether a mutation is present based on the result of the PCR. For this purpose, typically an ARMS-PCR is employed, in which case the forward primer may be an ARMS primer with the 3' most nucleotide being complementary to the mutant nucleotide to be detected in the genomic DNA and cDNA molecules. Optionally, a TaqMan probe hybridizing to a sequence in the genomic DNA flanked by the complementary sequence of the forward primer and the sequence of the reverse primer may also be used. If the mutant nucleotide is present, PCR reaction using the primer pair is allowed to happen, and fluorescent signal is emitted from the TaqMan probe. If the mutant nucleotide is absent, PCR reaction using the primer pair fails to take place and no fluorescent signal is produced.

In some embodiments, the invention includes a first pair of primers to complete the PCR using the genomic DNA as a template, and a second pair of primers to complete the PCR using a RNA molecule derived from the genomic DNA as a template. The first pair of primers includes a first forward primer and a first reverse primer, and the second pair of primers includes a second forward primer and a second reverse primer.

In one embodiments of the present invention, the first forward primer is an ARMS primer, and the reverse primer is a universal primer.

In another embodiment, the second forward primer is an ARMS primer, and the second reverse primer is a universal primer.

In a preferred embodiment of the present invention, the first pair of primers and the second pair of primers amplify the same portion of an exon of the human gene. Optionally, the first forward primer and the second forward primer are the same; the first reverse primer and the second reverse primer are the same.

As used herein, the term "ARMS primer" has the same meaning generally understood in the art, i.e., a primer with the 3' most nucleotide being complementary to the mutant nucleotide in the DNA template. A universal primer is a primer with a length of about 15-40 bases complementary to the other strand of the DNA template. In one embodiment of the present invention, the second and the third bases from the 3' end of the ARMS primer are mismatched bases, that is, not complementary to the bases in the DNA template. In one embodiments of the present invention, The Tm of the forward primer and the Tm of the reverse primer do not exceed 5° C.

When a probe is used in, e.g., a TaqMan PCR, a linear probe or a stem-loop probe may be used. Typically, the probe may be labeled with a detectable signal such as a radioisotope, fluorescein, biotin, an enzyme (e.g., alkaline phosphatase), an enzyme substrate, a ligand, or an antibody.

In one embodiment of the invention, the probe is labeled at one end with a fluorophore and at the other end with a quenching group. The fluorophore and quenching group of the probe are not limited and can be selected from the group consisting of FAM, HEX, VIC, ROX, CY5, BHQ, TAMRA and MGB, and the like. The probe sequence must be complementary to one strand or the other strand of the template sequence to be amplified by the PCR reaction.

When an ARMS primer is employed, a blocking DNA (or "blocker") may be used to increase the selectivity of mutant amplification, especially in a high background of wild-type DNA. A blocker is a DNA fragment with a length of 15-40 bases, with the 3' end nucleotide modified such that it cannot be used as a primer for DNA synthesis by Taq polymerase. In other words, nucleotide addition to the 3' end of the blocker is not allowed due to the modification. The blocker typically has a nucleotide sequence that overlaps with the forward ARMS primer and is capable of hybridizing to the wild type sequence surrounding the mutant nucleotide in the DNA template, but cannot substantially hybridize to the mutant sequence. In one embodiment of the invention, the Tm of the blocker is 4-7° C. higher than that of the primers and 5-10° C. lower than that of the probe. In one embodiment of the invention, at an appropriate annealing temperature, the blocker preferentially hybridizes to the wild-type gene sequence to block the hybridizing of the ARMS primer to the wild-type DNA template. This helps to ensure that the primer preferentially hybridizes to the mutant gene, thereby increasing the specificity of the PCR.

In the present invention, because the genomic DNA and the RNA molecules are in a mixture, in some embodiments, the reverse transcription for cDNA synthesis and the Taq polymerase-catalyzed PCR may take place in the same reaction tube and at about the same time. Thus, the method may employ an enzyme mixture having in admixture both a reverse transcriptase and a Taq polymerase.

Thus, in some embodiments, the method of the present invention comprises the steps of:

providing a mixture of nucleic acid molecules containing both a genomic DNA and RNA molecules derived from the genomic DNA; performing a reverse transcription reaction with a reverse transcriptase to provide cDNA molecules from the RNA molecules in the mixture; and performing PCR using both the genomic DNA and the cDNA molecules as templates. In the method, both the genomic DNA and the RNA molecules are extracted from a a biological sample. In the method, the step of performing PCR comprises:

providing a forward primer and a reverse primer, said forward primer being an ARMS primer with the 3' most nucleotide being complementary to the mutant nucleotide in the genomic DNA and cDNA molecules; providing a TaqMan probe hybridizing to a sequence in the genomic DNA flanked by the complementary sequence of the forward primer and the sequence of said reverse primer; and allowing PCR reaction to occur if said mutant nucleotide is present.

Alternatively, mutation detection is enabled by sequencing any amplified DNA molecules resulting from the step of performing PCR.

The CODAR-PCR method of the present invention can detect a trace amount of a mutation in both DNA and RNA from a whole blood sample using a small amount of sample. Combining sample extraction, amplicon selection, specific primers, blocker, and high-efficiency enzymes, the detection limit of a mutant in a background of wild-type molecules can reach 0.01% or lower (1 copy mutant gene can be detected from 10000 copies of wild gene) without non-specific amplification.

In accordance with a second aspect of the present invention, a PCR reaction mixture is provided that is an intermediate in the method of the present invention described above. The PCR reaction mixture comprises a mixture of nucleic acid molecules having both a genomic DNA of a human gene and a RNA molecule derived from the genomic DNA. Both the genomic DNA and the RNA molecule are extracted from a human whole blood sample from a cancer patient. The PCR reaction mixture further contains a reverse transcriptase, a Taq DNA polymerase, and a pair of PCR primers. In some embodiments, the reaction mixture also contains one or more of the followings: a blocker as described above, a TaqMan probe, dNTPs, buffer, an internal control primer pair, etc.

A third aspect of the present invention provides a kit for detecting a gene mutation in a biological sample. The kit comprises a first primer pair capable of amplifying by PCR a DNA sequence of a gene; a RT primer for priming reverse transcription from a RNA transcript of the DNA sequence to provide a cDNA; a second primer pair capable of amplifying by PCR all or part of said cDNA sequence; and an enzyme mixture having both a reverse transcriptase and a Taq polymerase. In some embodiments, the kit further includes one or more of the followings: a blocker as described above, a TaqMan probe, dNTPs, buffer, an internal control primer pair, nucleic acid extraction reagent preferably extracting both DNA and RNA, etc.

The method, reaction mixture, and kit of the present invention may be used with any biological samples from a patient such as a cancer patient. In one embodiment of the present invention, the biological sample is a plasma sample, a whole blood sample, a urine sample, fresh tissue sample or formaldehyde fixed paraffin embedded tissue sample. The cancer patients are patients having a tumor such as tumor in lung cancer, thyroid nodules, melanoma, or colorectal cancer tumor.

In some embodiments, the mutation to be detected is a mutation in e.g., the genes EGFR, ALK, ROS1, BRAF, KRAS, PIK3CA, p53, BRCA1, BRCA2, NTRK, IDH1, IDH2, etc. In one embodiment of the present invention, the human gene is EGFR. This gene has more than 29 types of mutations located in exon 18, exon 19, exon 20 and exon 21. In one embodiment, the human gene is EGFR, and the mutation may be anyone selected from the mutations located in exon 20. In another embodiment, the human gene is EGFR, and the mutation is T790M.

In one embodiments of the present invention, the human gene is ALK. This gene has 13 types of fusion mutations located on exon 20.

In one embodiments of the present invention, the human gene is ROS1. This gene has 15 types of fusion mutations located on exon 32, exon 34, exon 35 and exon 36.

In one embodiments of the present invention, the human gene is BRAF. In a more preferably embodiment of the present invention, the human gene is BRAF, and the mutation is V600E.

In one embodiments of the present invention, the human gene is KRAS. This gene has 7 types of fusion mutations located on codon 12 and codon 13.

The amplicon produced by the PCR reaction in the method of the present invention using the reaction mixture and the kit of present invention described above is preferably completely located in one exon, and both the genomic DNA and cDNA are amplified to produce the same one amplicon, at a length of about 100 base pairs or less, preferably, about 70 bp or less.

EXAMPLES

The following examples are used herein to demonstrate preferred embodiments of the invention. Those skilled in the art will appreciate that the techniques disclosed in the above examples are representative of the techniques discovered by the inventors that can be used to practice the invention and are therefore considered as a preferred embodiment of the invention. However, it will be apparent to those skilled in the art will appreciate that specific embodiments disclosed in the above examples can be modified a lot, still can obtain the same or the similar results without departing from the spirit or scope of the invention.

Unless defined otherwise, all technical and scientific terms used herein have the same meaning as commonly understood by those skilled in the art to which the invention pertains, and the materials cited herein and the materials they reference are incorporated by reference.

Many equivalents to the specific embodiments of the inventions described herein will be apparent to those skilled in the art. These equivalents will be included in the claims.

Example 1

Detection of the T790M Mutation of EGFR Gene by CODAR-PCR

1. Sample Preparation

The whole blood samples of the patients with advanced non-small cell lung cancer were selected either having T790M mutation of the EGFR gene or not. The DNA and the total nucleic acids (DNA and RNA) were extracted respectively from the plasma DNA or the whole blood after being processed. The original nucleic acids were detected after extraction. The detection information is shown as below.

| Blood sample | Sample type | Nucleic acid(s) |
|---|---|---|
| Whole blood with T790M mutation | Plasma | DNA |
|  |  | DNA and RNA |
| Whole blood without T790M mutation | Whole blood | DNA |
|  |  | DNA and RNA |

2. Amplicon Selection

An amplicon with 72 bases (SEQ ID NO: 1) was selected according to EGFR gene sequence with T790M mutation by querying the cosmic database.

```
                                          (SEQ ID NO: 1)
CCACCGTGCAGCTCATCATGCAGCTCATGCCCTTCGGCTGCCTCCTGGACT

ATGTCCGGGAACACAAAGACA
```

3. Primers, Probes, and Blocker

The designed primers, blocker and probes are shown as below:

```
Forward primer:
                                          (SEQ ID NO: 2)
CCACCGTGCAGCTCATAAT
```

```
Reverse primer:
                                          (SEQ ID NO: 3)
TGTCTTTGTTTCCCGGAC Probe:
                                          (SEQ ID NO: 4)
FAM-GCTCATGCCCTTCGG-MGB Blocker:
                                          (SEQ ID NO: 5)
CACCGTGCAGCTCATCACG-PHO Internal control forward primer:
                                          (SEQ ID NO: 6)
AAATCCTGCATGGCGC Internal control reverse primer:
                                          (SEQ ID NO: 7)
GCCACTGGATGCTCTCCA Internal control probe:
                                          (SEQ ID NO: 8)
VIC-AACAACCCTGCCCTGTG-MGB
```

4. Enzymes

The mixed enzymes are formed by mixing a reverse transcriptase and Taq DNA polymerases.

5. The System of the Fluorescence PCR is as Follows:

| Components | Amount (μL) |
|---|---|
| Mutate forward primer (100 μM) | 0.5 |
| Mutate reverse primer (100 μM) | 0.5 |
| Mutation probe (100 μM) | 0.5 |
| Internal control forward primer (100 μM) | 0.2 |
| Internal control reverse primer (100 μM) | 0.2 |
| Internal control probe (100 μM) | 0.2 |
| Blocker (100 μM) | 1.0 |
| Mixed enzymes | 1.25 |
| Buffer | 12.5 |
| Template | 5 |
| H2O | 3.15 |
| Total | 25 |

6. The Procedure of the PCR

PCR was performed on ABI 7500PCR apparatus with the procedure of:

First stage: 50° C., 10 minutes.

Second stage: 95° C., 1 minutes.

Third stage: 95° C., 15 seconds; 60° C. 30 seconds (collecting fluorescence signal), 50 cycles

COMPARATIVE EXAMPLE

1. Designed Primers and Probes

```
Forward primer:
                                          (SEQ ID NO: 9)
CCACCGTGCAGCTCATCAT Reverse primer:
                                          (SEQ ID NO: 10)
CCGTATCTCCCTTCCCTGATTAC
```

The probe and the internal control primers and probe were the same as the Sample example.

2. The System of the RT-qPCR is as Follows

| Components | Amount (μL) |
|---|---|
| Forward primer(100 μM) | 0.5 |
| Reverse primers (100 μM) | 0.5 |
| Probe (100 μM) | 0.5 |
| Internal control forward primer (100 μM) | 0.2 |
| Internal control reverse primer (100 μM)) | 0.2 |
| Internal control probe (100 μM) | 0.2 |
| Mixed enzymes | 1.25 |
| Buffer | 12.5 |
| Template | 5 |
| H₂O | 4.15 |
| Total | 25 |

Other conditions and operations were the same as the Sample examples in this Example.

The determination method of the result is as follows:

(1) Comparison between CODAR-PCR method and ordinary ARMS method.

For the positive sample, the smaller the Ct value, the higher the amplification efficiency and the higher the detection sensitivity. For the negative sample, the larger the Ct value, the higher the detection specificity.

(2) Comparison of types of the nucleic acid and the sample to be detected by CODAR-PCR method.

For different types of the nucleic acids, i.e. DNA, DAR (DNA and RNA) extracted from the positive samples, the smaller the Ct value, the higher the amplification efficiency and the higher the detection sensitivity. For different types of nucleic acids, i.e. DNA, DAR (DNA and RNA) extracted from the negative samples, the larger the Ct value, the higher the detection specificity.

The results are as follows:

(1) Ordinary ARMS method and the CODAR-PCR method were used to detect the peripheral blood samples from the patients with advanced non-small cell lung cancer. The detection results are shown in FIGS. 1, 2, 3, and 4. The amplification efficiency of the CODAR-PCR is better than the ordinary ARMS method. The Ct values by ARMS-PCR using the DNA and the DAR from the positive plasma sample were 42.965 and 42.274, respectively. In contrast, the Ct values by CODAR-PCR using the DNA and the DAR from the same positive plasma sample were 39.301, 37.498, respectively. The Ct values by ARMS-PCR using the DNA and the DAR from the whole blood sample were 38.970 and 36.304, respectively. These are contrasted with the Ct values of 37.301 and 35.476, respectively, when CODAR-PCR was used on the same sample. As can be seen from FIGS. 5, 6, 7 and 8, the detection specificity of the CODAR-PCR method is better than the ordinary ARMS method, too. The Ct values using the DNA and the DAR from the negative plasma and the DNA and the DAR from the negative whole blood by the ordinary ARMS method were 43.917, 40.397, 39.593 and 37.630, respectively. In contrast, there was no amplification signal, that is, no Ct value when the same negative samples were tested by the CODAR-PCR method.

(2) For the detection of positive blood samples by CODAR-PCR method, it can be seen from FIGS. 1, 2, 3 and 4 that, for the same type of the biological sample, the sensitivity of detection using the DAR is better than that using the DNA only. That is, the Ct values of the detections using the DNA only from the plasma and the whole blood were 39.704 and 37.301, respectively, whereas the Ct values of the detections using the DAR from the plasma and the whole blood were 37.498 and 35.476, respectively. In addition, regardless of using DNA only or DAR, the sensitivities in the whole-blood sample were higher than those in the plasma sample. The Ct values using the DNA and the DAR from the plasma were 39.704 and 37.498, respectively, whereas the Ct values using the DNA and the DAR from the whole blood were 37.301 and 35.476, respectively.

For the testing of negative blood samples by CODAR-PCR method, it can be seen from FIGS. 5, 6, 7 and 8 that, for the same type of the biological sample, there is no difference in detection specificity between DAR and DNA only as templates. Neither produced any Ct value. In addition, regardless of DNA only or DAR used, the detection specificities in the whole-blood sample have no difference from the specificities in the plasma sample. That is, there was no Ct value from the plasma and the whole blood using the DNA or the DAR therefrom as template.

Example 2

Detection of the V600E Mutation of BRAF Gene by CODAR-PCR

1. Sample Preparation

The formaldehyde fixed paraffin-embedded samples (FFPE samples) of the patients with melanoma were selected to have, either has V600E mutation of the BRAF gene or not. The DNA and DAR were extracted from the FFPE samples, respectively.

2. Amplicon Selection

An amplicon with 85 bases (SEQ ID NO: 11) located at exon 21 was selected according to BRAF gene sequence with V600E mutation by querying the cosmic database.

```
                                           (SEQ ID NO: 11)
GGTGATTTTGGTCTAGCTACAGAGAAATCTCGATGGAGTGGGTCCCATCAG

TTTGAACAGTTGTCTGGATCCATTTTGTGGATGG
```

3. Primers, Probes, and Blocker

The designed primers, blocker and probes are shown as below:

```
Forward primers:
                                           (SEQ ID NO: 12)
GGTGATTTTGGTCTAGCTACTGA Reverse primers:
                                           (SEQ ID NO: 13)
CCATCCACAAAATGGATCCAGAC probe:
                                           (SEQ ID NO: 14)
FAM-ATGGAGTGGGTCCCATCA-MGB Blocker:
                                           (SEQ ID NO: 15)
GGTGATTTTGGTCTAGCTACAGTGAAA-PHO Internal control forward primers:
                                           (SEQ ID NO: 16)
GTGGAATATCAAACAAATGATTAAG Internal control reverse primers:
                                           (SEQ ID NO: 17)
ATTGATGGTGGATTATGCTCC
```

-continued

```
Internal control probe:
                                      (SEQ ID NO: 18)
VIC-ACACAGGAACATATAGAGGC-MGB
```

4. Enzymes

The mixed enzymes are formed by mixing a reverse transcriptase and DNA polymerases.

5. Fluorescence PCR Amplification, the System is as Follows:

| Components | Amount (μL) |
|---|---|
| Mutate forward primer (100 μM) | 0.75 |
| Mutate reverse primer (100 μM) | 0.75 |
| Mutation probe (100 μM) | 0.5 |
| Internal control forward primer (100 μM) | 0.25 |
| Internal control reverse primer (100 μM) | 0.25 |
| Internal control probe (100 μM) | 0.25 |
| Blocker (100 μM) | 1.0 |
| Mixed enzymes | 1.5 |
| Buffer | 12.5 |
| Template | 5 |
| H$_2$O | 2.25 |
| Total | 25 |

6. PCR Reaction Procedure

PCR was performed on ABI 7500PCR apparatus with the procedure of:

First stage: 50° C., 15 minutes.

Second stage: 95° C., 10 minutes.

Third stage: 95° C., 10 seconds; 60° C. 34 seconds (collecting fluorescence signal), 45 cycles

COMPARATIVE EXAMPLE

1. Design Primers and Probe

```
Forward primer:
                                      (SEQ ID NO: 19)
GGTGATTTTGGTCTAGCTACAGA Reverse primer:
                                      (SEQ ID NO: 20)
CTTACCATCCACAAAATGGATCCAG
```

The probe and the internal control primers and probe were the same as the Sample example.

2. The RT-qPCR System is as Follows

| Components | Amount (μL) |
|---|---|
| Forward primer(100 μM) | 0.75 |
| Reverse primers (100 μM) | 0.75 |
| Probe (100 μM) | 0.5 |
| Internal control forward primer (100 μM) | 0.25 |
| Internal control reverse primer (100 μM) | 0.25 |
| Internal control probe (100 μM) | 0.25 |
| Mixed enzymes | 1.5 |
| Buffer | 12.5 |
| Template | 5 |
| H2O | 3.25 |
| Total | 25 |

Other conditions and operations were the same as the Sample examples in this Example.

The determination method of the result is as follows:

(1) Comparison between CODAR-PCR method and ordinary ARMS method.

For the positive sample, the smaller the Ct value, the higher the amplification efficiency and the higher the detection sensitivity. For the negative sample, the larger the Ct value, the higher the detection specificity.

(2) Comparison of types of the nucleic acid and the sample to be detected by CODAR-PCR method.

For different types of the nucleic acids, i.e. DNA, DAR (DNA and RNA) extracted from the positive samples, the smaller the Ct value, the higher the amplification efficiency and the higher the detection sensitivity. For different types of nucleic acids, i.e. DNA, DAR (DNA and RNA) extracted from the negative samples, the larger the Ct value, the higher the detection specificity.

Figure 1:
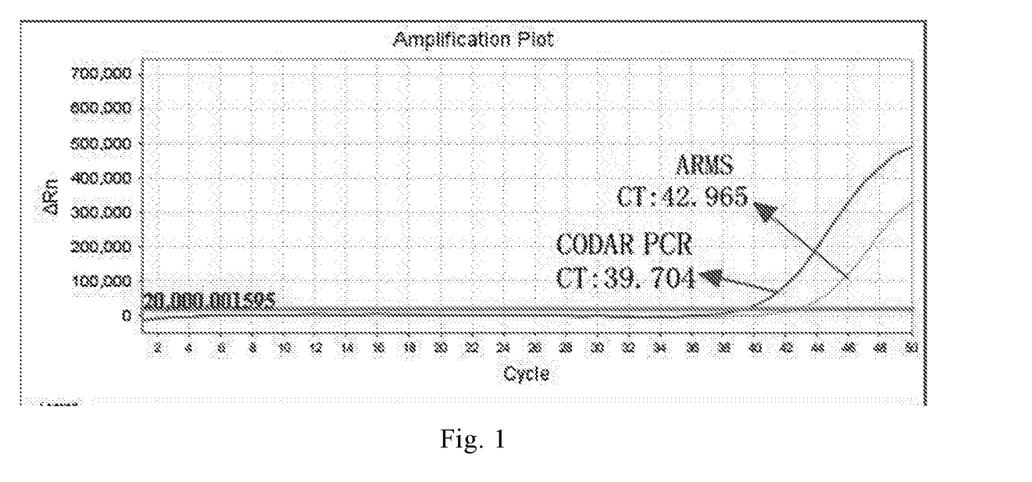
FIG. 1 shows the detection results by CODAR-PCR method and ordinary ARMS-PCR method using the DNA extracted from a mutant-positive plasma sample in Example 1.
Figure 2:
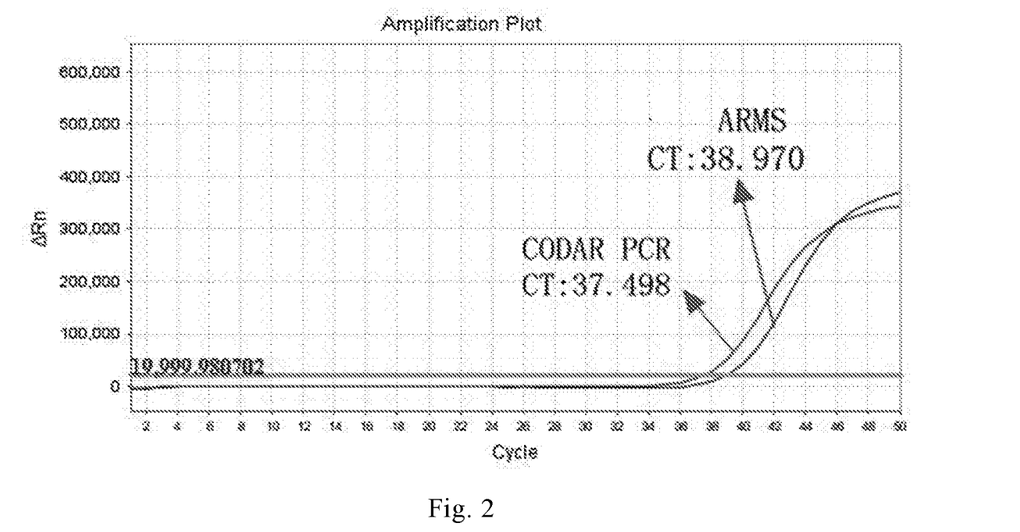
FIG. 2 shows the detection results by CODAR-PCR method and ordinary ARMS-PCR method using DNA and RNA extracted from a mutant-positive plasma sample in Example 1.
Figure 3:
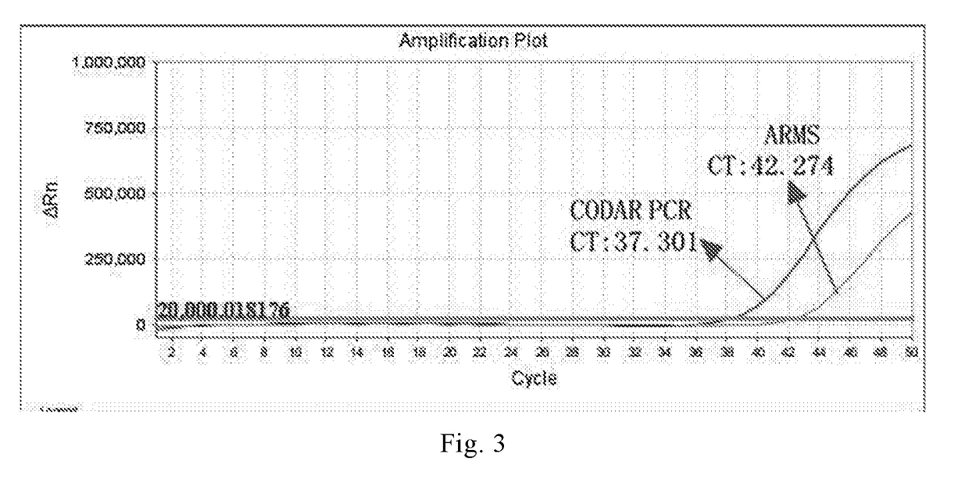
FIG. 3 shows the detection results by CODAR-PCR method and ordinary ARMS-PCR method using DNA extracted from a mutant-positive whole blood sample in Example 1.
Figure 4:
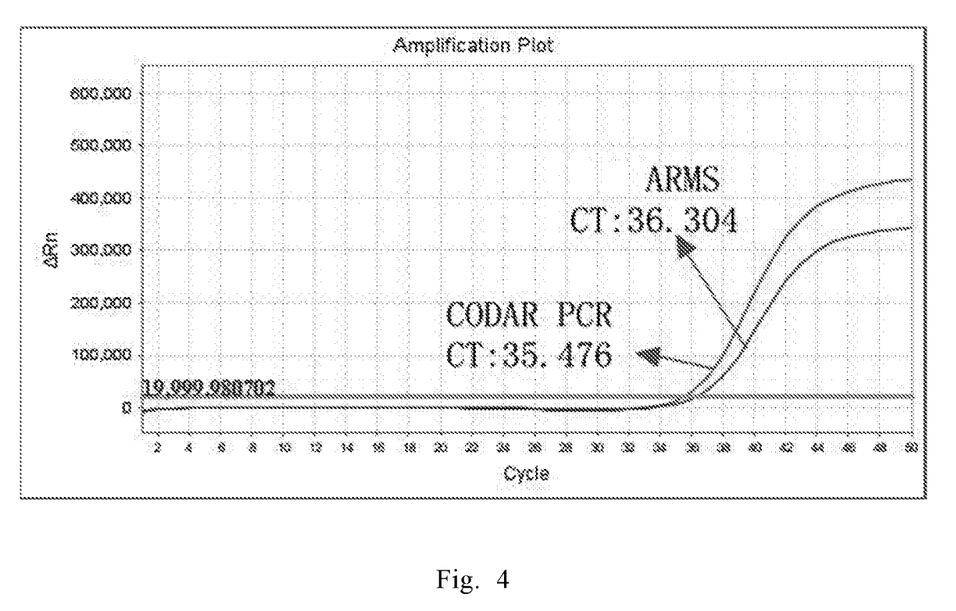
FIG. 4 shows the detection results by CODAR-PCR method and ordinary ARMS-PCR method using DNA and RNA extracted from a mutant-whole blood sample in Example 1.
Figure 5:
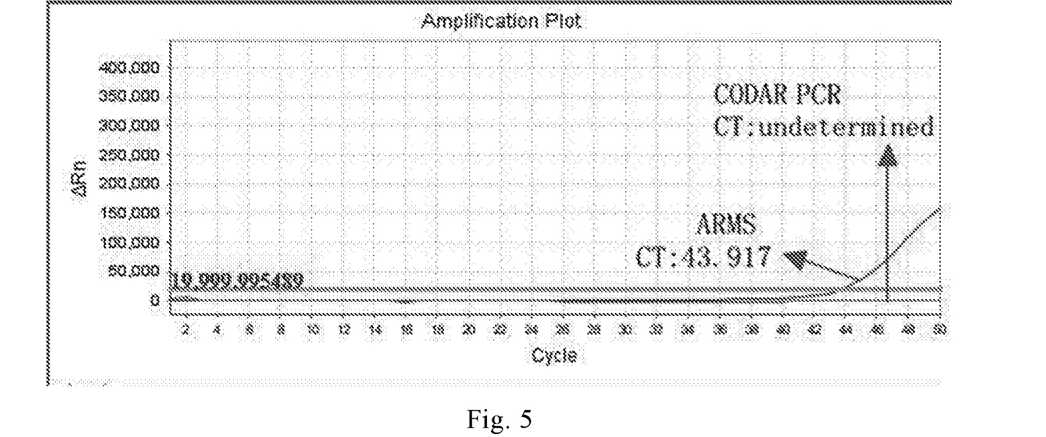
FIG. 5 shows the detection results of a mutant-negative plasma by CODAR-PCR method and ordinary ARMS method using DNA therefrom in Example 1.
Figure 6:
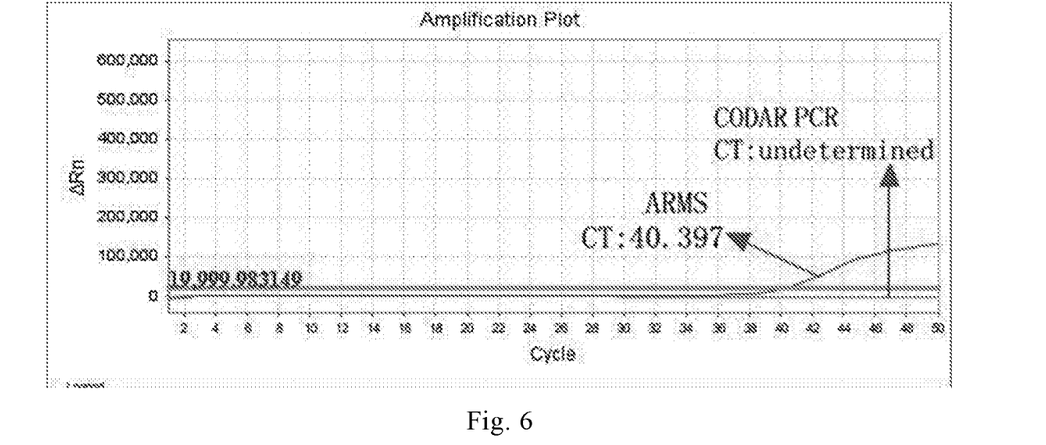
FIG. 6 shows the detection results of a mutant-negative plasma by CODAR-PCR method and ordinary ARMS method using DAR therefrom in Example 1.
Figure 7:
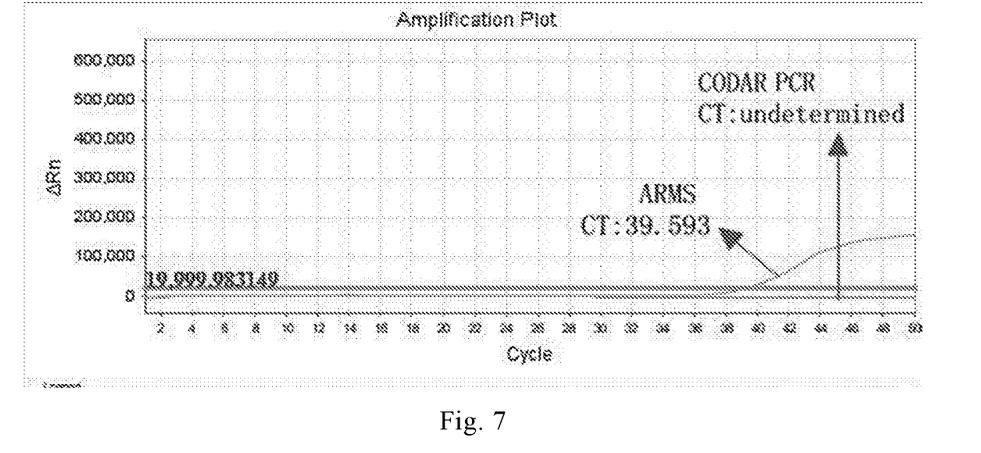
FIG. 7 shows the detection results of a mutant-negative whole blood by CODAR-PCR method and ordinary ARMS method using DNA therefrom in Example 1.
Figure 8:
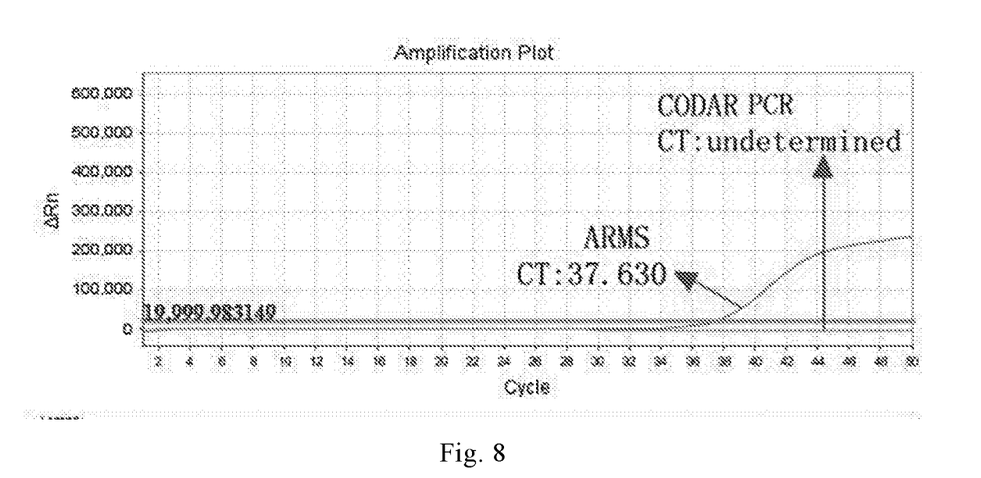
FIG. 8 shows the detection results of a mutant-negative whole blood by CODAR-PCR method and ordinary ARMS method using DAR therefrom in Example 1.
Figure 9:
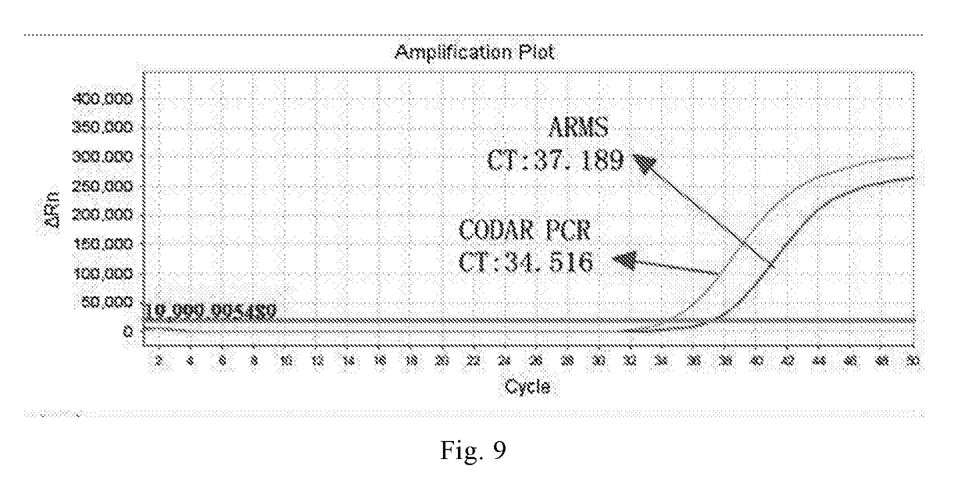
FIG. 9 shows the detection results of a mutant-positive FFPE tissue by CODAR-PCR method and ordinary ARMS method using DNA therefrom in Example 2.
Figure 10:
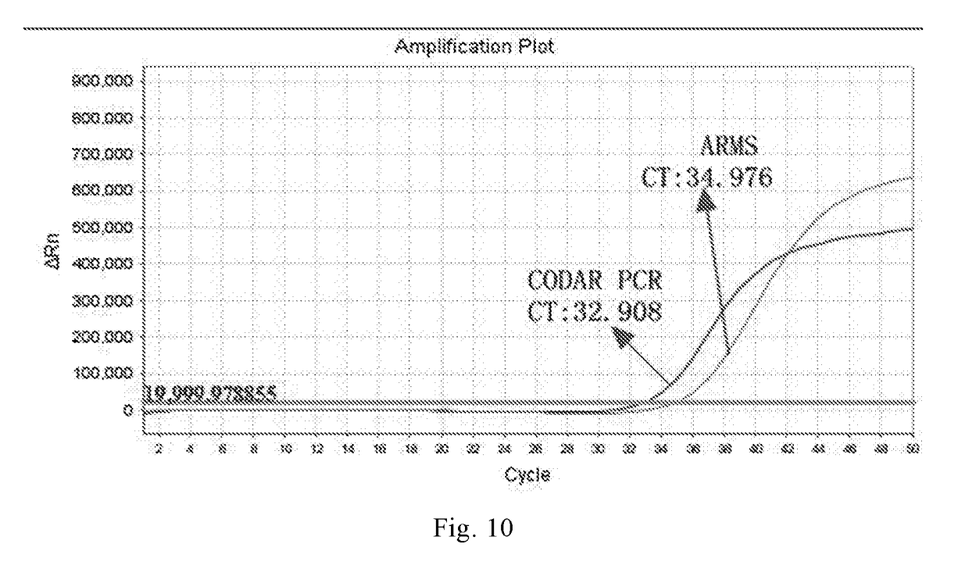
FIG. 10 shows the detection results of mutant-positive FFPE tissue by CODAR-PCR method and ordinary ARMS method using DAR therefrom in Example 2.
Figure 11:
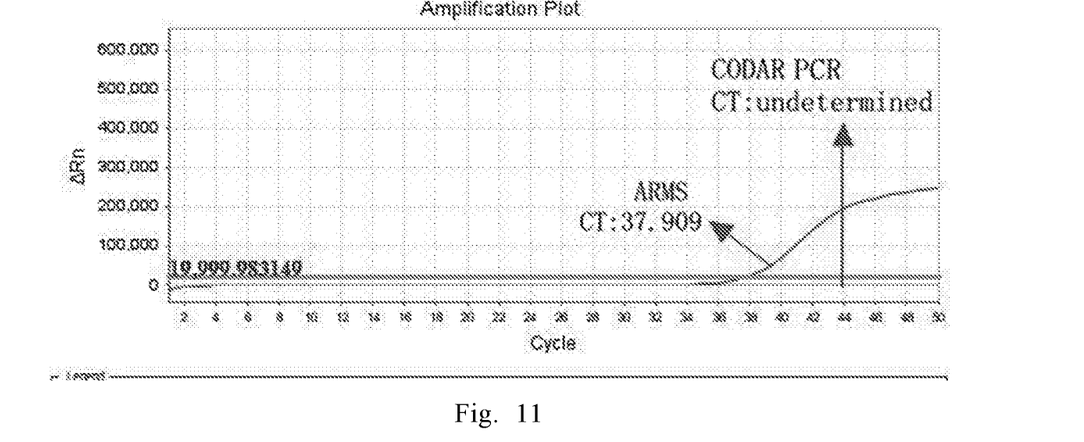
FIG. 11 shows the detection results of a mutant-negative FFPE tissue by CODAR-PCR method and ordinary ARMS method using DNA therefrom in Example 2.
Figure 12:
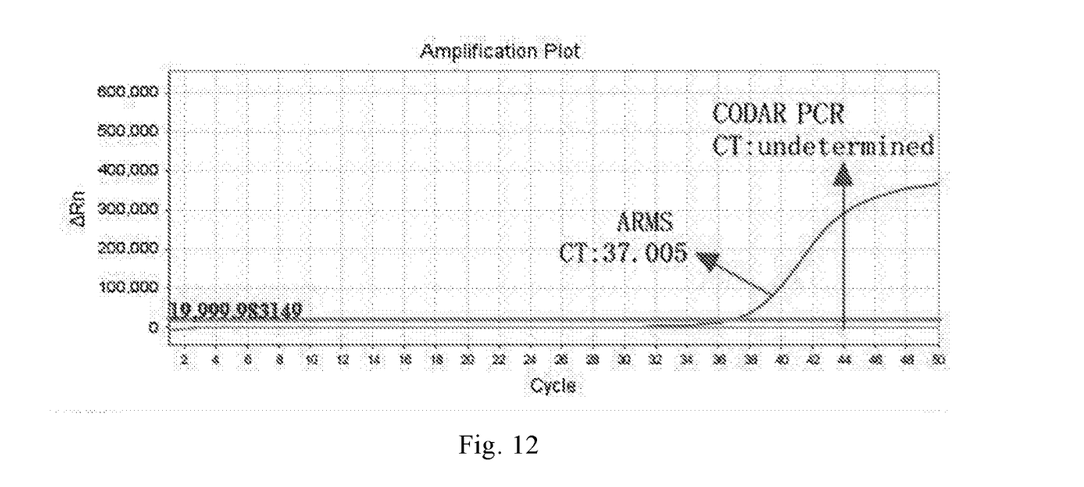
FIG. 12 shows the detection results of a mutant-negative FFPE tissue by CODAR-PCR method and ordinary ARMS method using DAR therefrom in Example 2.

The results are as follows:

(1) Ordinary ARMS method and the CODAR-PCR method were used to detect the FFPE melanoma samples, the detection results are showed as in FIGS. 9 and 10. The amplification efficiency of the CODAR-PCR is better than the ordinary ARMS method, because the Ct values of the detections using the DNA and the DAR by the ordinary ARMS method were 37.189 and 34.976, respectively, whereas the Ct values of the detections using the DNA and the DAR by the CODAR-PCR method were 34.516 and 32.908, respectively. As can be seen from FIGS. 11 and 12, the detection specificity of the CODAR-PCR method is better than the ordinary ARMS method, too. The Ct values of the detections using the DNA and the DAR by the ordinary ARMS method were 37.909 and 37.005, respectively. Whereas there was no amplification signal, that is, no Ct value when the negative samples were detected by the CODAR-PCR method.

(2) For the detection of positive samples by CODAR-PCR method, it can be seen from FIGS. 9 and 10 that, for the same type of the biological sample, the sensitivity of detection using the DAR is better than that using DNA only. That is, the Ct value of the detection using DNA only was 34.516 whereas the Ct value of the detection using DAR was 32.908. In addition, as can be seen from FIGS. 11 and 12 that, using DNA only or DAR, the detection specificities of the same sample have no difference from each other. That is, there was no Ct value when detected the FFPE sample using the DNA or the DAR therefrom.

All documents mentioned in the present application are hereby incorporated by reference in their entireties as if the disclosures in In addition, it is to be understood that various modifications and changes may be made by those skilled in the art in the form of the appended claims.

We claim:

1. A method for detecting a mutation in a biological sample, comprising: providing a mixture of nucleic acid molecules comprising both a genomic DNA and a RNA molecule derived from said genomic DNA, both said genomic DNA and said RNA molecule being extracted from a human whole blood sample from a cancer patient;
   performing a reverse transcription reaction with a reverse transcriptase to provide cDNA molecules from said RNA molecule in said mixture; and
   performing PCR using both said genomic DNA and said cDNA molecules as templates,
   determining whether a mutation is present based on the result of the PCR.

2. The method of claim 1, further comprising sequencing any amplified DNA molecules resulting from said step of performing PCR.

3. The method of claim 1, wherein the step of performing PCR comprises: providing a forward primer and a reverse primer, said forward primer being an ARMS primer with the 3' most nucleotide being complementary to the mutant nucleotide in said genomic DNA and cDNA molecules;
   providing a TaqMan probe hybridizing to a sequence in said genomic DNA flanked by the complementary sequence of said forward primer and the sequence of said reverse primer; and
   allowing PCR reaction to occur if said mutant nucleotide is present.

4. A PCR reaction mixture, comprising:
   a mixture of nucleic acid molecules comprising both a genomic DNA of a human gene and a RNA molecule derived from said genomic DNA, both extracted from a human whole blood sample from a cancer patient, in admixture with;
   a reverse transcriptase,
   a Taq DNA polymerase, and
   a pair of PCR primers,
   wherein one primer of said pair of PCR primers is an ARMS primer.

5. The PCR reaction mixture of claim 4, further comprising a TaqMan probe.

6. A kit for detecting a gene mutation in a biological sample, comprising:
   a first primer pair capable of amplifying by PCR a DNA sequence of a gene;
   a RT primer for priming reverse transcription from a RNA transcript of said DNA sequence to provide a cDNA;
   a second primer pair capable of amplifying by PCR all or part of said cDNA sequence; and
   an enzyme mixture having both a reverse transcriptase and a Taq polymerase,
   wherein one primer of said second primer pair is an ARMS primer.

* * * * *